United States Patent [19]

Hirota et al.

[11] Patent Number: 4,479,893
[45] Date of Patent: Oct. 30, 1984

[54] SHAMPOO COMPOSITION CONTAINING PHOSPHORIC ACID ESTER AND ORGANIC SILICON DERIVATIVE

[75] Inventors: Hajime Hirota, Tokyo; Hiroshi Watanabe, Funabashi, both of Japan

[73] Assignee: Kao Corporation, Tokyo, Japan

[21] Appl. No.: 418,361

[22] Filed: Sep. 15, 1982

[30] Foreign Application Priority Data

Oct. 28, 1981 [JP] Japan .................. 56-172460

[51] Int. Cl.$^3$ .................. C11D 1/16; C11D 1/82; C11D 1/83
[52] U.S. Cl. .................. 252/542; 252/174.15; 252/174.16; 252/174.17; 252/545; 252/546; 252/547; 252/548; 252/550; 252/551; 252/555; 252/DIG. 13
[58] Field of Search .................. 252/174.15, 174.17, 252/545, DIG. 13, 548, 550, 551, 555, 542, 547, 546, 174.16

[56] References Cited

U.S. PATENT DOCUMENTS

| | | | |
|---|---|---|---|
| 2,826,551 | 3/1958 | Geen .................. | 252/174.15 |
| 3,957,970 | 5/1976 | Korkis .................. | 424/70 |
| 3,992,332 | 11/1976 | Zenon .................. | 252/548 |
| 4,185,087 | 1/1980 | Morlino .................. | 424/70 |
| 4,259,204 | 3/1981 | Homma .................. | 252/174.16 |
| 4,298,494 | 11/1981 | Parslow et al. .................. | 252/174.16 |
| 4,321,256 | 3/1982 | Hasegawa et al. .................. | 424/70 |
| 4,363,755 | 12/1982 | Uchino et al. .................. | 252/545 |
| 4,364,837 | 12/1982 | Pader .................. | 252/173 |

FOREIGN PATENT DOCUMENTS

| | | |
|---|---|---|
| 167799 | 12/1981 | Japan . |
| 849433 | 9/1960 | United Kingdom . |
| 1034782 | 7/1966 | United Kingdom . |

*Primary Examiner*—Prince E. Willis
*Attorney, Agent, or Firm*—Flynn, Thiel, Boutell & Tanis

[57] ABSTRACT

A shampoo composition is disclosed comprising a shampoo base containing:
(A) 0.1 to 5 wt. % of a phosphate ester surfactant of general formula (1):

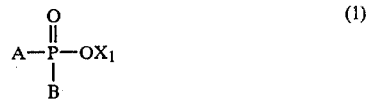

wherein A represents

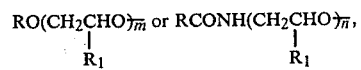

in which R represents a straight-chain or branched-chain, saturated or unsaturated hydrocarbyl group, $R_1$ represents a hydrogen or methyl group, m represents a number of 0 to 6, n represents a number of 1 to 6, B represents —$OX_2$ or A, $X_1$ and $X_2$ each represent hydrogen, alkali metal, alkyl($C_1$–$C_3$)-substituted ammonium, hydroxyalkyl($C_1$–$C_3$) group-containing alkanolamine or basic amino acid, and (B) 0.01 to 5 wt. % of a silicon derivative.

6 Claims, No Drawings

SHAMPOO COMPOSITION CONTAINING PHOSPHORIC ACID ESTER AND ORGANIC SILICON DERIVATIVE

The present invention relates to a hair shampoo composition. More particularly, the present invention relates to a hair shampoo composition containing a shampoo base, such as an anionic surfactant, to which are added a phosphate ester surfactant and a silicon derivative.

Conventional hair shampoo compositions contain, as a shampoo base, an anionic surfactant, such as an alkyl sulfate salt or polyoxyethylene alkyl sulfate salt, a nonionic surfactant, such as a polyoxyethylene alkyl ether or fatty acid alkanolamide, or an amphoteric surfactant, such as an alkyl betaine or alkyl amine oxide. These shampoo bases have been used either singly or in the form of mixtures thereof. However, if shampoo compositions containing only these shampoo bases are used, excessive removal of sebum or oil from the hair occurs during washing, whereby the washed hair has a poor feel and easy combing or brushing of the hair becomes impossible. Further, after complete drying, the hair cannot be dressed well. Particularly in winter, when the ambient humidity is low, static electricity is generated by brushing, thereby causing a hair-flying phenomenon and tangles, and making smooth combing and brushing more difficult, resulting in split hairs or worn hairs. For the purpose of overcoming these problems, there has been employed a method wherein an oil is incorporated in a shampoo base. However, the amount of oil that can be contained in such a shampoo is limited. Generally, the oil contained in the shampoo is emulsified or solubilized by a surfactant. Thus, it has been difficult to leave a sufficient amount of the oil on the scalp or hair.

If a large amount of an oil is incorporated in a shampoo, the essential properties of the shampoo, such as its foaming power and deterging power, are deteriorated seriously and its commercial value is reduced greatly, even though the adsorption of the oil onto the hair is increased. Recently, there have been proposed various shampoo compositions containing a cationic polymer or the like, added for the purpose of improving the rinsing effects on the washed hair. However, many of these shampoos have defects. For example, some of them have a poor foaming property and low deterging power, and they become colored or discolored with time, although they do exhibit a hair conditioning effect. Others have a poor hair conditioning effect and are high in cost, which is a serious disadvantage, although they have an excellent foaming property.

After intensive investigations made for the purposes of overcoming the defects of conventional shampoo compositions and developing a shampoo composition having conditioning effects for obtaining soft, smooth-feeling hair after shampooing, the inventors have discovered that if the combination of a phosphate ester surfactant and a silicon derivative is incorporated in an otherwise conventional shampoo base selected from the group consisting of anionic surfactants (excluding phosphate ester surfactants), nonionic surfactants and amphoteric surfactants, and mixtures thereof, excellent conditioning effects can be obtained, and the shampooed hair is soft and smooth to the touch and can be easily combed, without deterioration of the essential hair washing functions of the shampoo composition. The present invention has been completed on the basis of this discovery.

The present invention provides a shampoo composition comprising a shampoo base that is an anionic, nonionic, or amphoteric surface active agent, or a mixture of two or more thereof, said shampoo base containing:

(A) 0.1 to 5 wt.% of a phosphate ester surfactant of general formula (1):

wherein A represents

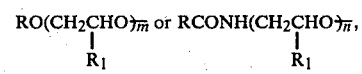

in which R represents a straight-chain or branched-chain, saturated or unsaturated hydrocarbyl group having 8 to 22 carbon atoms, $R_1$ represents hydrogen or a methyl group, m represents an integer of from 0 to 6, n represents an integer of from 1 to 6, B represents $-OX_2$ or $-A$, and $X_1$ and $X_2$, which can be the same or different, each represent hydrogen, alkali metal, alkyl($C_1$-$C_3$)-substituted ammonium, hydroxyalkyl($C_1$-$C_3$) group-containing alkanolamine or a basic amino acid, and (B) 0.01 to 5 wt.% of a silicon derivative.

As the anionic surfactants (excluding phosphate ester surfactants), nonionic surfactants and amphoteric surfactants useful as the shampoo base composition according to the present invention, the following materials can be utilized:

(A) Anionic surfactants:

(1) straight-chain or branched-chain alkylbenzenesulfonates having an alkyl group containing an average of 10 to 16 carbon atoms, (2) alkyl- or alkenyl-ethoxysulfates having a straight-chain or branched-chain alkyl or alkenyl group having an average of 8 to 20 carbon atoms, and adducted with an average of 0.5 to 8 mols of ethylene oxide, per mol thereof, (3) alkyl- or alkenyl-sulfates having alkyl or alkenyl groups having an average of 10 to 20 carbon atoms, (4) olefinsulfonates containing an average of 10 to 20 carbon atoms in the molecule, (5) alkanesulfonates having an average of 10 to 20 carbon atoms in the molecule, (6) saturated or unsaturated fatty acid salts having an average of 10 to 20 carbon atoms in the molecule, (7) alkyl- or alkenyl-ethoxycarboxylates having alkyl or alkenyl groups containing an average of 10 to 20 carbon atoms, and adducted with an average of 0.5-8 mols of ethylene oxide, per mol thereof, (8) α-sulfofatty acid salts or esters of the formula:

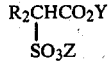

wherein Y represents an alkyl group of 1 to 3 carbon atoms or a counter ion of the anionic surfactant, Z represents a counter ion of the anionic surfactant and $R_2$ represents an alkyl or alkenyl group of 10 to 20 carbon atoms, and (9) succinic acid derivatives of the formula:

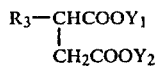

wherein $R_3$ represents an alkyl or alkenyl group of 6 to 20 carbon atoms, and $Y_1$ and $Y_2$ each represent a counter ion.

As the counter ions of the above-mentioned anionic surfactants, there can be used ions of alkali metals, such as sodium and potassium, alkaline earth metals, such as calcium and magnesium, ammonium, alkanolamines containing 1 to 3 alkanol groups of 2 to 3 carbon atoms each such as monoethanolamine, diethanolamine, triethanolamine and triisopropanolamine, and basic amino acids such as lysine and arginine. Among these counter ions, sodium, ammonium or triethanolamine ions are preferred as the counter ion.

(B) Nonionic surfactants:

(1) polyoxyethylene alkyl or alkenyl ethers having alkyl or alkenyl groups of 8 to 20 carbon atoms on the average, and containing 3 to 12 mols of ethylene oxide added thereto, per mol thereof, (2) polyoxyethylene alkylphenyl ethers having alkyl groups of 8 to 12 carbon atoms on the average, and having 3 to 12 mols of ethylene oxide added thereto, per mol thereof, (3) higher fatty acid alkanolamides or alkylene oxide adducts thereof of the formula:

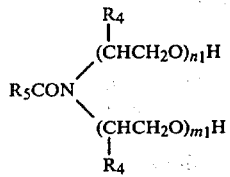

wherein $R_4$ represents H or $CH_3$, $R_5$ represents an alkyl or alkenyl group of 10 to 20 carbon atoms, $n_1$ represents an integer of 1 to 3 and $m_1$ represents an integer of 0 to 3, (4) polyoxypropylene alkyl or alkenyl ethers having alkyl or alkenyl groups of 10 to 20 carbon atoms on the average, and having 1 to 20 mols of propylene oxide added thereto, per mol thereof, (5) polyoxybutylene alkyl or alkenyl ethers having alkyl or alkenyl groups of 10 to 20 carbon atoms on the average, and having 1 to 20 mols of butylene oxide added thereto, per mol thereof, (6) nonionic surfactants having alkyl or alkenyl groups of 10 to 20 carbon atoms on the average, and having 1 to 30 total mols of ethylene oxide and propylene oxide or ethylene oxide and butylene oxide, the ratio of ethylene oxide to propylene oxide or butylene oxide being 0.1:9.9 to 9.9:0.1, added thereto, per mol thereof, and (7) sucrose/fatty acid esters comprising a fatty acid of 10 to 20 carbon atoms on the average and sucrose.

(C) Amphoteric surfactants:

(1) alkylamine oxides of the formula:

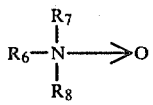

wherein $R_6$ represents an alkyl or alkenyl group of 10 to 20 carbon atoms, and $R_7$ and $R_8$ are the same or different and represent alkyl groups of 1 to 3 carbon atoms, (2) alkyl betaines or sulfobetaines of the formula:

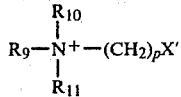

wherein $R_9$ represents an alkyl or alkenyl group of 10 to 20 carbon atoms, $R_{10}$ and $R_{11}$ represent an alkyl group of 1 to 4 carbon atoms, p represents an integer of 1 to 3 and X' represents a $-COO^-$ or $-SO_3^-$ group, (3) imidazoline-type amphoteric surfactants of the formula:

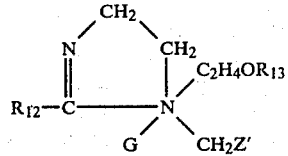

wherein $R_{12}$ represents a fatty acid radical of 10 to 20 carbon atoms, $R_{13}$ represents hydrogen, sodium or $CH_2COOMe$, Z' represents $-COOM$, $-CH_2COOM$ or

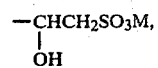

wherein M is sodium, hydrogen or organic base, G represents $-OH$, an acid salt or an anionic surfactant sulfate or sulfonate, and (4) amidoamine compounds of the formula:

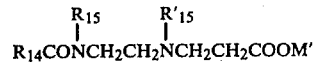

wherein $R_{14}$ represents a saturated or unsaturated, aliphatic hydrocarbyl group of 7 to 21 carbon atoms, $R_{15}$ represents a hydrogen atom or hydroxyalkyl group of 1 to 4 carbon atoms and $R'_{15}$ has the same definition as $R_{15}$ or represents $-CH_2CH_2COOM'$, M' being a hydrogen atom, alkali metal salt, ammonium salt or alkanolamine salt.

Among the above-mentioned shampoo bases, those particularly preferred are anionic surfactants such as straight-chain or branched-chain alkylsulfuric acid ester salts of 10 to 16 carbon atoms, polyoxyethylene alkylsulfuric acid ester salts (average ethylene oxide addition mol number: 0.5–8) in which the alkyl group has 8 to 20 carbon atoms on the average, olefinsulfonic acid salts of 10 to 16 carbon atoms on the average, nonionic surfactants such as higher fatty acid mono- or dialkanolamides having an alkyl group of 10 to 14 carbon atoms on the average, and amphoteric surfactants of alkyl amine oxide, alkyl betaine and imidazoline types having 10 to 14 carbon atoms on the average. The shampoo bases can be used either singly or in the form of a mixture of two or more of them, in a concentration in the range of 5 to 30% (by weight; the same shall apply for concentrations given hereafter), preferably 10 to 25% by weight.

The phosphate ester surfactants used in the present invention are represented by the above general formula (1). As alkali metals for $X_1$ and $X_2$ in the general formula (1), there can be employed, for example, lithium, potassium and sodium. When the substituents $X_1$ and $X_2$ in the formula (1) are the alkyl($C_1$-$C_3$)-substituted ammonium group or alkanolamine group containing a hydroxyalkyl group of 1 to 3 carbon atoms, such compounds are obtained in the step of producing the anionic phosphate ester salt of general formula (1) wherein an amine used for neutralizing a corresponding phosphoric acid is quaternized into a corresponding cation after the neutralization. The amine is a primary, secondary or tertiary amine having alkyl group(s) of 1 to 3 carbon atoms, which alkyl groups can have a hydroxyl group. The amines include, for example, dimethylmonoethanolamine, methyldiethanolamine, trimethylamine, triethylamine, dipropylamine, propyldimethylamine, monoethanolamine, diethanolamine, triethanolamine, isopropyldimethylamine and isopropylethanolamine. Preferred amines are monoethanolamine, diethanolamine and triethanolamine. Among them, triethanolamine is particularly preferred. As the basic amino acids, there can be used, for example, lysine and arginine.

As preferred examples of the phosphate ester surfactants according to the present invention, there can be mentioned those of the above general formula (1) wherein A represents $$RO(CH_2CHO)_m,$$
$$|$$
$$R_1$$

R being a straight-chain or branched-chain, alkyl group. The weight ratio of the monophosphate ester (B is $OX_2$) to the diphosphate ester (B is A) is preferably 100/0 to 50/50, particularly 80/20 to 60/40. Especially preferred phosphate ester surfactants are sodium or triethanolamine (TEA) salts of alkyl($C_{12-18}$) phosphates and polyoxyethylene (addition mol number: $\overline{P}$=1.0–3.0) alkyl($C_{12-18}$)phosphates.

The phosphate ester surfactants are used either alone or in the form of a mixture of two or more thereof in an amount of 0.1 to 5 wt.%, preferably 0.3–3 wt.%, based on the total weight of the shampoo composition. If more than 5% of the phosphate surfactant is incorporated in the shampoo composition, the foam will be undesirably sticky.

As examples of the silicon derivatives used in the present invention, the following compounds can be mentioned:

(1) dimethylpolysiloxane:

$$(CH_3)_3SiO[(CH_3)_2SiO]_{3\sim650}Si(CH_3)_3$$

(2) methylphenylpolysiloxane:

$$(CH_3)_3SiO\left(\begin{array}{c}C_6H_5\\ \diagdown\\ \diagup\\ CH_3\end{array}SiO\right)_{1\sim500}Si(CH_3)_3 \text{ or}$$

$$(CH_3)_3SiO[(CH_3)_2SiO]_a[(C_6H_5)_2SiO]_bSi(CH_3)_3$$

wherein the sum of a+b is 1 to 500, (3) polyether-modified silicone:

$$(CH_3)_3SiO[(CH_3)_2SiO]_{x_1}[CH_3SiO]_{y_1}Si(CH_3)_3$$
$$|$$
$$(CH_2)_3$$
$$|$$
$$O-(C_2H_4O)_{m_2}-(C_3H_6O)_{n_2}-A'$$

wherein A' represents an alkyl group of 1 to 12 carbon atoms or hydrogen, $x_1$ represents an integer of 1 to 100 (preferably 3 to 30), $y_1$ represents an integer of 1 to 50 (preferably 1 to 30), $m_2$ represents an integer of 1 to 50 (preferably 3 to 30) and $n_2$ represents an integer of 0 to 50 (preferably 0 to 30), with the proviso that the sum of $x_1$ and $y_1$ is at least 15 and the sum of $m_2$ and $n_2$ is at least 5, (4) epoxy-modified silicone:

$$(CH_3)_3SiO[(CH_3)_2SiO]_{x_2}[CH_3SiO]_{y_2}Si(CH_3)_3$$
$$|$$
$$R_{16}CH\text{——}CH_2$$
$$\diagdown\diagup$$
$$O$$

wherein $x_2$ represents an integer of 1 to 500 (preferably 1 to 250), $y_2$ represents an integer of 1 to 50 (preferably 1 to 30) and $R_{16}$ represents an alkylene group of 1 to 3 carbon atoms, (5) fluorine-modified silicone:

$$(CH_3)_3SiO(CH_3SiO)_{x_3}Si(CH_3)_3$$
$$|$$
$$(CH_2)_2$$
$$|$$
$$CF_3$$

wherein $x_3$ represents an integer of 1 to 400 (preferably 1 to 250), (6) alcohol-modified silicone:

$$HO(CH_2)R_{17}-[(CH_3)_2SiO]_{x_4}(CH_3)_2SiR_{17}-CH_2OH$$

or $$(CH_3)_3SiO[(CH_3)_2SiO]_{x_4}(CH_3SiO)_{y_4}Si(CH_3)_3$$
$$|$$
$$R_{17}-CH-OH$$
$$|$$
$$CH_3$$

wherein $x_4$ and $y_4$ each represent an integer of 1 to 500 (preferably 1 to 200) and $R_{17}$ represents $-C_nH_{2n}-$ (n being an integer of from 0 to 4), and (7) alkyl-modified silicone:

$$(CH_3)_3SiO(CH_3SiO)_{x_5}(CH_3SiO)_{y_5}Si(CH_3)_3$$
$$\underset{R_{18}}{|} \quad \underset{R'_{18}}{|}\text{—C}_6H_5$$

wherein $x_5$ and $y_5$ each represent an integer of 1 to 500 (preferably 1 to 200), $R_{18}$ represents an alkyl group of 2 to 18 carbon atoms and $R'_{18}$ represents $—C_nH_{2n}—$, n being an integer of from 0 to 4, or $$(CH_3)_3SiO[(CH_3)_2SiO]_{x_6}(CH_3SiO)_{y_6}Si(CH_3)_3$$
$$\underset{R_{19}}{|}$$

wherein $x_6$ and $y_6$ each represent an integer of 1 to 500 (preferably 1 to 200) and $R_{19}$ represents an alkyl group of 10 to 16 carbon atoms.

In the above-mentioned silicon derivatives, the polyether-modified silicones, epoxy-modified silicones and alcohol-modified silicones are preferred. The polyether-modified silicones are most preferred.

The silicone derivatives are used either singly or in the form of a mixture of two or more of them, in a total amount of 0.01 to 5 wt.%, preferably 0.05 to 3 wt.%, based on the total weight of the shampoo composition. If the silicone derivative is used in an amount of less than 0.01 wt.%, the intended effects cannot be obtained, while if it is used in an amount of more than 5 wt.%, the foaming properties of the shampoo are seriously deteriorated.

The composition of the present invention should be in the form of a paste or a liquid containing water as the liquid medium, wherein the pH of the liquid is preferably 4 to 8.

The shampoo composition of the present invention can contain, in addition to the above-mentioned critical components, additives conventionally incorporated in hair shampoo compositions, such as a solubilizer, e.g. propylene glycol, glycerol or urea, a viscosity modifier, e.g. ethanol, an inorganic salt, higher alcohol, hydroxyethylcellulose or hydroxypropylcellulose, as well as a perfume, dyestuff, U.V. absorber, antioxidant, dandruff remover, germicide and antiseptic.

The following examples further illustrate the present invention, but these examples by no means limit the scope of the invention.

In the following examples, the performance assessments were made by the following test methods:

(1) Foaming test method:
0.5 wt.% of lanolin, as an artificial soil, was added to a 1% aqueous solution of a shampoo composition. The mixture was stirred with a flat propeller at 1000 rpm, with the direction of rotation being reversed at 10 sec intervals, at 40° C., for 5 min, in a cylinder. 30 sec after completion of the stirring, the quantity of the foam was measured.

(2) Feel of foam:
30 g of human hair was wetted with water at 40° C. to impregnate the same with 20 g of water. Then, the hair was shampooed, using 1 g of a shampoo composition. The feel of the foam was judged according to an organoleptic test by 20 female panelists.

Assessment properties:
Smoothness of finger passage through the hair during shampooing was judged as the "slipperiness of the foam". The appearance of the foam was judged from the viewpoint of its creaminess.

Criteria of the assessment:
O: Slipperiness of foam was higher than that of the standard composition, or the foam had a more creamy appearance.
X: Equivalent to the standard composition.

Composition of the standard composition:

| | |
|---|---|
| Sodium salt of polyoxyethylene (3) laurylsulfuric acid | 15 wt. % |
| Coconut fatty acid diethanolamide | 3 wt. % |
| Perfume | 0.3 wt. % |
| Water | balance |
| (pH 7.2) | |

(3) Ease of combing:
30 g of human hair was shampooed by shaking in 10 cc of a 10% aqueous solution of a shampoo composition at 40° C. for about 30 sec. Then, it was washed with running water for 1 min and squeezed. The hair was set in a strain gauge and combed. The load applied to the hair in the wet condition, during combing, was measured. Separately, the human hair washed with running water, as described above, was squeezed, dried with a dryer and left to stand in an air-conditioned room at 25° C. under a relative humidity of 65% overnight. The hair thus treated was set in a strain gauge and combed. The load applied to the hair in the dry condition, during combing, was measured.

The lower the load, the easier is the combing.

(4) Hair flying:
During the drying step, in the test for ease of combing, the change of the state of the hair due to build-up of static electricity was observed macroscopically.

O: Hair flying was not caused at all.
X: Hair flying was observed.

EXAMPLE 1

The shampoo compositions shown in Table 1 were prepared by a conventional method and the effects of the critical components were examined. The results shown in Table 1 were obtained.

TABLE 1

| | | Sample No. | | | | | | | | | | | |
|---|---|---|---|---|---|---|---|---|---|---|---|---|---|
| | | (Invention) | | | | | | (Comparison) | | | | | |
| | | 1 | 2 | 3 | 4 | 5 | 6 | 7 | 8 | 9 | 10 | 11 | 12 |
| Components (wt. %) | Sodium polyoxyethylene(3) laurylsulfate | 15 | 15 | 15 | 15 | 15 | 15 | 15 | 15 | 15 | 15 | 15 | 15 |
| | Sodium polyoxyethylene(3) laurylphosphate | 1 | | | | | | 0.05 | 6 | 1 | 1 | | 1 |
| | Triethanolamine laurylphosphate | | 1 | | | | | | | | | | |
| | Sodium polyoxyethylene(4) oleylphosphate | | | 1 | | | | | | | | | |
| | Lauroylamidoethylpolyoxyethylene(5) phosphoric acid | | | | 1 | | | | | | | | |
| | Polyoxypropylene(5) cetyl ether | | | | | 1 | | | | | | | |

TABLE 1-continued

| | | Sample No. | | | | | | | | | | |
|---|---|---|---|---|---|---|---|---|---|---|---|---|
| | | (Invention) | | | | | | (Comparison) | | | | |
| | | 1 | 2 | 3 | 4 | 5 | 6 | 7 | 8 | 9 | 10 | 11 | 12 |
| | phosphoric acid | | | | | | 1 | | | | | | |
| | Triethanolamine oleylcetylphosphate | | | | | | | | | | | | |
| | Polyether-modified silicone* | 1 | 1 | 1 | 1 | 1 | 1 | 1 | 1 | 0.005 | 6 | 1 | |
| | Water | Balance | Balance | Balance | Balance | Balance | Balance | Balance | Balance | Balance | Balance | Balance | Balance |
| Properties | Foaming Properties | Foaming (m) | 187 | 189 | 193 | 193 | 193 | 189 | 190 | 139 | 176 | 182 | 197 | 160 |
| | | Slipperiness of foam | 0 | 0 | 0 | 0 | 0 | 0 | X | X | X | 0 | X | X |
| | | Creaminess | 0 | 0 | 0 | 0 | 0 | 0 | X | X sticky | X | X | X | X |
| | Finish | Degree of ease of combing (under a wet condition) (g) | 184 | 182 | 180 | 186 | 184 | 188 | 448 | 352 | 524 | 180 | 488 | 566 |
| | | Degree of ease of combing (under a dry condition) (g) | 80 | 72 | 76 | 82 | 86 | 84 | 324 | 278 | 326 | 78 | 296 | 358 |
| | | Hair flying | 0 | 0 | 0 | 0 | 0 | 0 | X | 0 | X | 0 | X | X |

*Polyether-modified silicone:

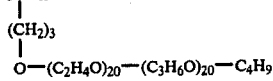

$(CH_3)_3SiO[(CH_3)_2SiO]_{20}[CH_3SiO]_3Si(CH_3)_3$
$|$
$(CH_2)_3$
$|$
$O-(C_2H_4O)_{20}-(C_3H_6O)_{20}-C_4H_9$

EXAMPLE 2

The following shampoo compositions were prepared and effects of the silicon derivatives were examined. The results shown in Table 2 were obtained:

Shampoo composition:

| | |
|---|---|
| Triethanolamine alkylsulfate | 16 wt. % |
| Coconut fatty acid diethanolamide | 3 wt. % |
| Triethanolamine polyoxyethylene (2.5) laurylphosphate | 1 wt. % |
| Silicon derivative (polyether-modified silicone) | (see Table 2) |
| Perfume | 0.3 wt. % |
| Water | balance |
| pH | 7.0 |

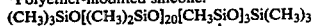
$\overline{C} = 12.5$, a derivative of an alcohol synthesized by the oxo method.

TABLE 2

| Sample No | Polyether-modified silicone* | | | | | Amount wt. (%) | Foaming (m) | Ease of combing (g) | | Hair flying |
|---|---|---|---|---|---|---|---|---|---|---|
| | x | y | m | n | A | | | wet | dry | |
| 13 | 20 | 5 | 20 | 20 | $C_8H_{17}$ | 0.5 | 200 | 176 | 74 | 0 |
| 14 | 5 | 20 | 10 | 0 | H | 0.5 | 193 | 182 | 76 | 0 |
| 15 | 20 | 5 | 45 | 4 | $C_3H_7$ | 0.5 | 203 | 206 | 98 | 0 |
| 16 | 150 | 20 | 25 | 10 | $C_8H_{17}$ | 0.5 | 111 | 178 | 76 | 0 |
| 17 | 20 | 5 | 3 | 0 | H | 0.5 | 104 | 183 | 96 | 0 |

*Polyether-modified silicone:

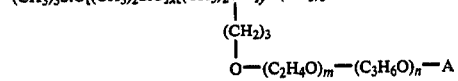

$(CH_3)_3SiO[(CH_3)_2SiO]_x[(CH_3)_2SiO]_ySi(CH_3)_3$
$|$
$(CH_2)_3$
$|$
$O-(C_2H_4O)_m-(C_3H_6O)_n-A$

EXAMPLE 3

The shampoo compositions of the present invention shown in Table 3 exhibited a high degree of combing ease and did not cause hair flying.

TABLE 3

| Sample No. | 18 | 19 | 20 | 21 | 22 |
|---|---|---|---|---|---|
| Sodium polyoxyethylene (3) lauryl ether sulfate | 12 | | | 5 | |
| Triethanolamine laurylsulfate | | 15 | | 5 | |
| Sodium olefinsulfonate ($C_{12-16}$) | | | 12 | | 5 |
| Lauric acid diethanolamide | 3 | | 4 | 2 | |
| Lauryldimethylamine oxide | | 3 | | | 3 |
| Miranol C2M* | | | | 8 | |

TABLE 3-continued

| Sample No. | 18 | 19 | 20 | 21 | 22 |
|---|---|---|---|---|---|
| Polyether-modified silicone** | 0.3 | 0.5 | 1.0 | 2.0 | 1.0 |
| Lauryl phosphate (mono/di = 30/70) | 0.8 | | 0.5 | | 2.0 |
| Polyoxypropylene (5) polyoxyethylene (1) cetyl ether phosphate | | 1.0 | | 2.0 | |

*Imidazoline-type amphoteric surfactant, a product of Miranol Chemical Co., U.S.A.
**The same silicone as used in Example 1.

The amounts in the above table are given in % by weight. The balance of the compositions was water and the pH was adjusted to pH 7.0.

EXAMPLE 4

The following shampoo compositions were prepared and applied to the hair of 20 long-haired female panelists in the shampooing test. The organoleptic test results are shown in Table 4.

| Shampoo A (present invention): | |
|---|---|
| Triethanolamine laurylsulfate | 18.0 wt. % |
| Triethanolamine laurylphosphate (mono/di = 70/30) | 1.0 wt. % |
| Polyether-modified silicone (the same as used in Example 1) | 0.5 wt. % |
| Methylcellulose* | 1.0 wt. % |
| Perfume | 0.3 wt. % |
| Water | balance |
| Shampoo B (comparative example): | |
| Triethanolamine laurylsulfate | 18.0 wt. % |
| Triethanolamine laurylphosphate (mono/di = 70/30) | 1.0 wt. % |

-continued

| | |
|---|---|
| Methylcellulose* | 1.0 wt. % |
| Perfume | 0.3 wt. % |
| Water | balance |
| Shampoo C (comparative example): | |
| Triethanolamine laurylsulfate | 18.0 wt. % |
| Polyether-modified silicone (the same as used in Example 1) | 0.5 wt. % |
| Methylcellulose* | 1.0 wt. % |
| Perfume | 0.3 wt. % |
| Water | balance |

*Methylcellulose was used in the form of a 2% aqueous solution thereof having a viscosity at 25° C. of 4000 cP.

TABLE 4

| | Judgment of Panelists | | | |
|---|---|---|---|---|
| | Shampoo A was the best | Shampoo B was the best | Shampoo C was the best | No answer |
| Creaminess of foam | 17 | 0 | 3 | 0 |
| Smoothness of finger passage through the hair during shampooing | 16 | 0 | 2 | 2 |
| Feel after shampooing (under a wet condition) | 18 | 1 | 1 | 0 |
| Feel after shampooing (under a dry condition) | 19 | 0 | 0 | 1 |
| Ease of dressing of hair | 16 | 1 | 1 | 2 |

80–90% of the panelists recommended shampoo A for the respective properties.

We claim:

1. A hair shampoo composition consisting essentially of an aqueous shampoo base consisting essentially of 10 to 25 wt.% of one or a mixture of two or more surface active agents selected from the group consisting of straight-chain or branched-chain alkylsulfuric acid ester salts of 10 to 16 carbon atoms, polyoxyethylene alkylsulfuric acid ester salts having an average ethylene oxide addition mol number in the range of 0.5–8 in which the alkyl group has 8 to 20 carbon atoms on the average, olefinsulfonic acid salts of 10 to 16 carbon atoms on the average, higher fatty acid mono- and dialkanolamides having an alkyl group of 10 to 14 carbon atoms on the average, alkyl amine oxides, alkyl betaines and imidazolines having 10 to 14 carbon atoms on the average, said agents being effective for washing hair, and the balance is essentially water, said shampoo base having incorporated therein (A) 0.1 to 5.0 wt.%, based on the total weight of the shampoo composition, of at least one anionic phosphoric acid ester having the formula

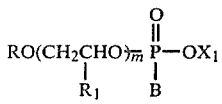

in which R is linear or branched alkyl group having 8 to 22 carbon atoms; $R_1$ is hydrogen or methyl; m is an integer of 0 to 6; B is $-OX_2$ or

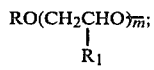

and $X_1$ and $X_2$, which can be the same or different, are hydrogen, alkali metal, alkyl($C_1$–$C_3$)-substituted ammonium, hydroxyalkyl($C_1$–$C_3$)-containing alkanolamine or a basic amino acid, said phosphoric acid ester consisting essentially of a mixture of monoester wherein B is $-OX_2$ and diester wherein B is

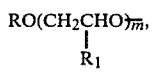

such that the weight ratio of said monoester to said diester is in the range of 100/0 to 50/50; and (B) 0.01 to 5 wt.%, based on the total weight of the shampoo composition, of a polyether-modified silicone having the formula:

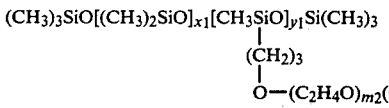

wherein A' is alkyl of 1 to 12 carbon atoms or hydrogen, $x_1$ is an integer of from 1 to 100, $y_1$ is an integer of from 1 to 50, $m_2$ is an integer of 1 to 50 and $n_2$ is an integer of 0 to 50, with the proviso that the sum of $x_1$ and $y_1$ is at least 15 and the sum of $m_2$ and $n_2$ is at least 5.

2. A shampoo composition according to claim 1, wherein $X_1$ and $X_2$ are selected from the group consisting of lithium, potassium, sodium, monoethanolamine, diethanolamine, triethanolamine, lysine and arginine.

3. A shampoo composition as claimed in claim 1, wherein said shampoo base contains 0.3 to 3 wt.% of (A) and 0.05 to 3 wt.% of (B).

4. A shampoo composition according to claim 1, wherein the ratio of said monoester to said diester is in the range of 80/20 to 60/40, and said phosphoric acid ester is selected from the group consisting of sodium and triethanolamine salts of alkyl($C_{12}$–$C_{18}$) phosphates and polyoxyethylene alkyl($C_{12}$–$C_{18}$) phosphates having a polyoxyethylene addition mol number of from 1.0 to 3.0.

5. A hair shampoo composition as claimed in claim 1, wherein said surface active agents are selected from the group consisting of sodium polyoxyethylene (3) lauryl sulfate, triethanolamine alkylsulfate, sodium ($C_{12}$–$C_{16}$) olefinsulfonate, lauric acid diethanolamide, lauryldimethylamine oxide, and mixtures thereof.

6. A hair shampoo composition as claimed in claim 1, wherein m is greater than 0.

* * * * *